(12) United States Patent
Lin

(10) Patent No.: US 9,657,401 B2
(45) Date of Patent: May 23, 2017

(54) GAS GENERATOR FOR HEALTH USE

(71) Applicant: Hsin-Yung Lin, Shanghai (TW)

(72) Inventor: Hsin-Yung Lin, Shanghai (TW)

( * ) Notice: Subject to any disclaimer, the term of this patent is extended or adjusted under 35 U.S.C. 154(b) by 80 days.

(21) Appl. No.: 14/227,338

(22) Filed: Mar. 27, 2014

(65) Prior Publication Data
US 2014/0374243 A1 Dec. 25, 2014

(30) Foreign Application Priority Data
Jun. 19, 2013 (CN) .......................... 2013 1 0244278

(51) Int. Cl.
| | |
|---|---|
| *C25B 1/04* | (2006.01) |
| *C25B 9/06* | (2006.01) |
| *A61M 16/12* | (2006.01) |
| *A61M 16/16* | (2006.01) |
| *A61M 16/14* | (2006.01) |
| *C25B 15/08* | (2006.01) |
| *C25B 9/00* | (2006.01) |
| *A61M 21/02* | (2006.01) |
| *A61M 15/08* | (2006.01) |
| *A61M 21/00* | (2006.01) |

(52) U.S. Cl.
CPC ............... *C25B 9/06* (2013.01); *A61M 16/12* (2013.01); *A61M 16/122* (2014.02); *A61M 16/125* (2014.02); *A61M 16/14* (2013.01); *A61M 16/16* (2013.01); *A61M 21/02* (2013.01); *C25B 1/04* (2013.01); *C25B 9/00* (2013.01); *C25B 15/08* (2013.01); *A61M 15/08* (2013.01); *A61M 2021/0016* (2013.01); *A61M 2202/0208* (2013.01); *A61M 2205/8231* (2013.01); *Y02E 60/366* (2013.01)

(58) Field of Classification Search
CPC C25B 9/06; C25B 1/04; A61M 16/12; A61M 16/122; A61M 16/125
See application file for complete search history.

(56) References Cited

U.S. PATENT DOCUMENTS

| | | |
|---|---|---|
| 3,917,520 A | 11/1975 | Katz et al. |
| 5,445,722 A | 8/1995 | Yamaguti et al. |
| 5,520,858 A | 5/1996 | Yamaguchi et al. |
| 2003/0136402 A1 | 7/2003 | Jiang et al. |
| 2009/0014901 A1* | 1/2009 | Spiegelman ............ B01B 1/005 261/128 |
| 2010/0089395 A1 | 4/2010 | Power et al. |
| 2010/0181190 A1 | 7/2010 | Romaniuk |

(Continued)

FOREIGN PATENT DOCUMENTS

| | | |
|---|---|---|
| CN | 2496880 Y | 6/2002 |
| CN | 102068743 A | 5/2011 |

(Continued)

*Primary Examiner* — Nicholas A Smith
(74) *Attorney, Agent, or Firm* — Foster Pepper PLLC

(57) ABSTRACT

A gas generator for health use is provided. The gas generator for health use includes an electrolysis device for electrolyzing water and producing a gas mixture that includes hydrogen and oxygen. The gas generator for health use further includes a gas mixing system coupled to the electrolysis device to receive the gas mixture. The gas mixing system is adapted to mix the gas mixture with water vapor, an atomized medicinal liquid, a volatile essential oil or a combination thereof to produce a health gas for being inhaled by a user.

16 Claims, 2 Drawing Sheets

(56) References Cited

U.S. PATENT DOCUMENTS

| | | |
|---|---|---|
| 2010/0187128 A1 | 7/2010 | Neubert et al. |
| 2011/0048454 A1 | 3/2011 | Saeki et al. |
| 2011/0057455 A1 | 3/2011 | Russo et al. |
| 2011/0121735 A1 | 5/2011 | Penny |
| 2013/0092558 A1 | 4/2013 | Kim et al. |
| 2013/0112550 A1 | 5/2013 | Marsh et al. |
| 2013/0206586 A1 | 8/2013 | Lin |
| 2014/0318979 A1 | 10/2014 | Cronin et al. |
| 2015/0144132 A1* | 5/2015 | Satoh ................ A61M 16/0057 128/202.26 |

FOREIGN PATENT DOCUMENTS

| | | | |
|---|---|---|---|
| CN | 102488951 A | 6/2012 | |
| CN | 202576577 U | 12/2012 | |
| CN | 202576577 U | 12/2012 | |
| CN | 102847213 A | 1/2013 | |
| JP | 5091364 B1 | 9/2012 | |
| JP | 5100911 B1 | 12/2012 | |
| JP | WO 2014024984 A1 * | 2/2014 | ............ A61M 16/12 |
| RU | 2033815 C1 | 4/1995 | |
| RU | 2237044 C1 | 9/2004 | |
| RU | 2311859 C2 | 12/2007 | |

\* cited by examiner

GAS GENERATOR FOR HEALTH USE

PRIORITY CLAIM

This application claims the benefit of the filing date of China Patent Application No. 201310244278.9, filed Jun. 19, 2013, entitled "GAS GENERATOR FOR HEALTH USE," and the contents of which is hereby incorporated by reference in its entirety.

FIELD OF THE INVENTION

The present invention relates to a gas generator for health use, more particularly, to a gas generator that can produce a mixed gas of hydrogen and oxygen.

BACKGROUND OF THE INVENTION

From ancient times till now, humanity has always made preserving life a high priority. Many developments in medical technology are used for diseases and increasing life expectancy. In the past, most medical treatment was passive. In other words, diseases are treated only when people fall ill, by performing surgical operation, medication, chemotherapy, radiation treatment and so on. But recently, many medical experts are focusing on disease prevention, such as studying on the health effects of food, and screening for genetic disorders to actively reduce the risk of falling ill. Furthermore, to increase life expectancy, many anti-aging technologies have been developed, including skin care products and antioxidant food/medicine.

In recent years, people have been noticing the benefits of aromatherapy. Aromatherapy is a natural way to make people feel relaxed and become healthy. Essential oils are extracted from aromatic plants to act as a medium which is then exposed to someone by massaging, bathing, perfuming and so on. This method has existed since the ancient times of Egypt and is now gaining a lot of attention in Europe. A French scientist named RenéMaurice Gattefossé published his research results on aromatherapy in a scientific journal, which sparked interest in many people. His research found that the plant's essential oils can reach deep layer tissues of skin, which is then absorbed by blood vessels and to reach organs that need to be treated by blood circulation.

Therefore, the present invention proposed is a gas generator for health use. The gas generator can produce health gas for health care that makes people feel relaxed and is also suitable for medical treatment.

SUMMARY OF THE INVENTION

The present invention proposes a gas generator for health use. According to one aspect of the invention, the gas generator for health use can produce a gas mixture of hydrogen and oxygen for being inhaled by a user.

According to another aspect of the invention, the gas generator for health can produce a gas mixture that includes hydrogen and oxygen, mixed with atomized medicine, water vapor, volatile essential oil or a combination thereof, for being inhaled by a user.

According to an embodiment of the invention, a gas generator for health use is provided, comprising an electrolysis device used for electrolyzing water to produce a gas mixture of hydrogen and oxygen; and a gas mixing system, coupled to the electrolysis device for receiving the gas mixture and mixing the gas mixture with an atomized gas selected from a group consisting of water vapor, an atomized medicine, a volatile essential oil or a combination thereof to produce a health gas for being inhaled by a user.

According to another embodiment of the invention, the gas generator for health use further comprises a gas feeding element, coupled between the electrolysis device and the gas mixing system for feeding a gas to the gas mixture to reduce the concentration of hydrogen in the gas mixture, wherein the added gas is selected from a group consisting of air, water vapor, an inert gas or a combination thereof.

According to another embodiment of the invention, the gas generator for health use further comprises a flow meter, coupled to the electrolysis device for detecting the flow rate of the gas mixture of oxygen and hydrogen, thereby controlling the produced quantity of the gas mixture from the electrolysis device. The gas mixing system further comprises: a humidifier, coupled to the electrolysis device for receiving the gas mixture to produce a filtered gas; and an atomized/volatile gas mixing tank, coupled to the humidifier for receiving the filtered gas and producing the health gas through mixing the atomized/volatile gas and the filtered gas.

According to another embodiment of the invention, the gas generator for health use further comprises a conversion valve, coupled between the humidifier and the atomized/volatile gas mixing tank, wherein the conversion valve is adapted for selectively connecting the humidifier and the atomized/volatile gas mixing tank, so that the atomized gas and the filtered gas are mixed to produce the health gas, or selectively disconnecting the humidifier from the atomized/volatile gas mixing tank, so that the filtered gas is directly output. And the humidifier further comprises a pure water tank, into which the gas mixture may be introduced for filtering to produce the filtered gas. The atomized/volatile gas mixing tank further comprises an oscillator for atomizing or vaporizing a liquid to produce the atomized gas. The liquid is selected from a group consisting of an essential oil, a medicinal liquid, pure water or a combination thereof. The atomized gas is selected from a group consisting of a volatile essential oil, an atomized medicinal liquid, atomized water or a combination thereof. The user can adjust the composition of the health gas by switching ON/OFF the oscillator. For example, when the oscillator is switched on, the health gas will be produced by mixing the atomized gas and the filtered gas. And when the oscillator is switched off, the health gas will comprise only the filtered gas.

According to the invention, the gas generator for health use can produce a gas mixture of hydrogen and oxygen, optionally mixed with an atomized medicinal liquid, atomized water or a volatile essential oil, for being inhaled by a user. The presence of the hydrogen in the health gas would improve the anti-oxidation and anti-aging activity in the user who has inhaled the health gas. Furthermore, the health gas comprises the atomized medicinal liquid prescribed by a medical doctor, thereby facilitating the uptake of the medicinal liquid by the user. Moreover, the health gas, comprising the volatile essential oil, would allow the user to feel relaxed and become healthier.

Many other advantages and features of the present invention will be further understood by the following detailed description and the appended drawings.

BRIEF DESCRIPTION OF THE DRAWINGS

Some of the embodiments will be described in detail, with reference to the following figures, wherein like designations denote like members, wherein.

DETAILED DESCRIPTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Figure 1:
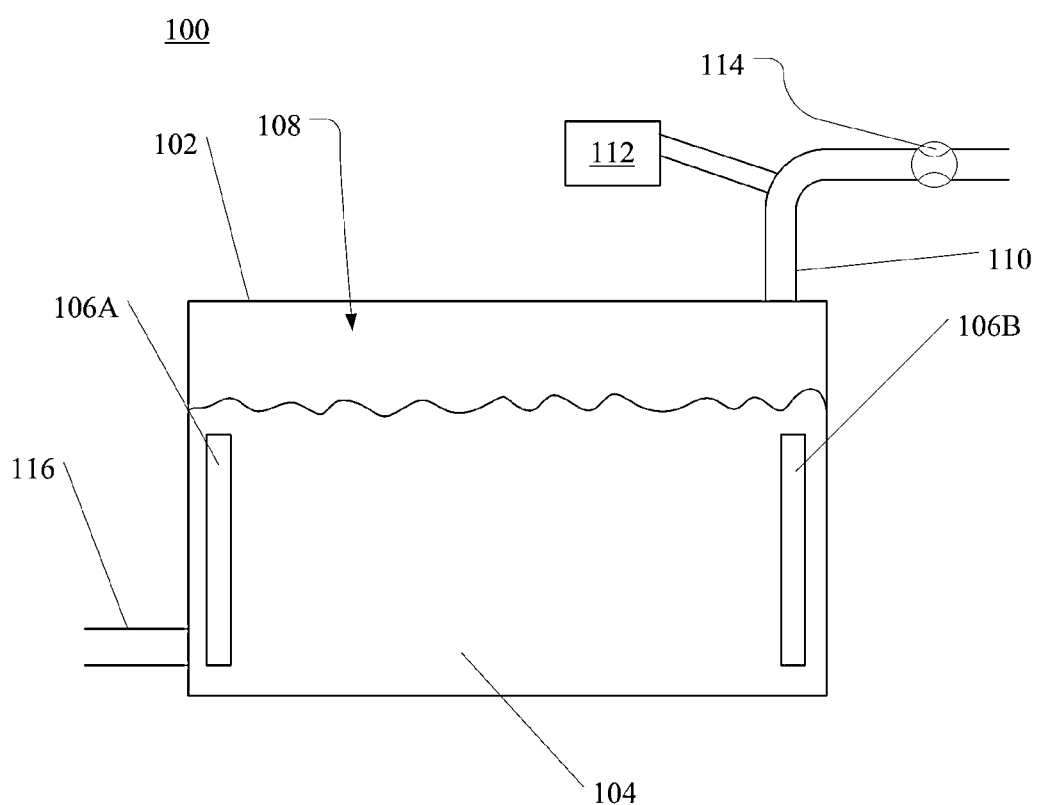
FIG. 1 is a schematic diagram of the electrolysis device in the gas generator for health use according to an embodiment of the invention.

Please refer to FIG. 1, which is a schematic diagram of the electrolysis device in the gas generator for health use according to a preferred embodiment of the invention. In the present invention, the health gas is a gas mixture comprising at least oxygen and hydrogen. In some embodiments, the gas mixture of hydrogen and oxygen can be produced by electrolyzing water. In some embodiments, the electrolysis device 100 comprises an electrolysis tank 102, used for containing electrolytic water 104 as shown in FIG. 1. The electrolytic water 104 is mainly pure water, optionally added with electrolytes, such as sodium hydroxide, calcium carbonate, sodium chloride and so on, depending on actual needs. The electrolysis tank 102 is further provided with two electrodes 106A, 106B, one being a positive electrode and the other being a negative electrode. The electrodes 106A, 106B are coupled to a power supply (not shown) for supplying power for electrolyzing water. In some embodiments, the electrodes 106A, 106B have fixed polarity. For example, the electrode 106A is an anode and the electrode 106B is a cathode. In other embodiments, electrodes 106A, 106B have interchangeable polarity. For example, the electrode 106A is an anode and the electrode 106B is a cathode at one moment and when a period of time passes, the electrode 106A is switched to a cathode and the electrode 106B is switched to an anode.

The electrolytic water 104 contained in the electrolysis tank 102 will begin electrolyzing when passed through the electrodes 106A, 106B. The hydrogen will be produced at the negative electrode (namely, the cathode) and the oxygen will be produced at the positive electrode (the anode). Moreover, the hydrogen and the oxygen will be liberated at the top of the electrolysis tank 102 and then become a gas mixture 108 that includes hydrogen and oxygen. The gas mixture 108 is output via a gas line 110 for future use. In other embodiments, the hydrogen produced at the negative electrode and the oxygen produced at the positive electrode are withdrawn from the electrolysis tank 102 via separate gas lines and mixed afterwards to produce the gas mixture 108. Because the ratio of hydrogen to oxygen produced by electrolyzing the electrolytic water 104 is nearly 2:1, the percentage of hydrogen may be over 66%. In other embodiments, an additional gas may be introduced into the gas mixture 108 by the gas feeding element 112, so as to reduce the concentration of hydrogen in the gas mixture 108 to an amount, for example, between 2% to 60%, such as an amount between 2% to 4%. Moreover, the added gas could be air, an inert gas (such as nitrogen), oxygen, water vapor, or a combination thereof. In other embodiments, a flow meter 114 is mounted in the gas line 110 and used for detecting the gas flow rate. The level of voltage or current (the power) supplied to the electrolysis tank 102 are adjusted based on the gas flow rate, thereby controlling the quality of the gas mixture 108 produced. As a result, when the gas mixture 108 is transferred to a downstream device and mixed with the gas in the downstream device, the concentration of the hydrogen is reduced. The term "adjusted" mentioned above is intended to encompass the case where the voltage or the current supplied to the electrolysis tank 102 is cut off (For example, when an abnormal value is detected by the flow meter 114, such as when the value is too high or too low, the flow meter 114 can be programmed to cut off the voltage or the current supplied to the electrolysis tank 102). It is worth noting that the gas feeding element 112 and the flow meter 114 are optional. In other words, the two elements (that is, the flow meter 114 and the gas feeding element 112) can be incorporated or not incorporated in the gas generator disclosed herein independently. Alternatively, the two elements can be replaced with other types of equipment capable of reducing the concentration of hydrogen. Moreover, the electrolysis tank 102 further comprises an input line 116 used for replenishing the electrolytic water 104 in the electrolysis tank 102. In other embodiments, the flow meter 114 in the gas line 110 is selectively replaced with a flow controller that controls the quality of the gas mixture 108 produced. The concentration of hydrogen will then be reduced by mixing the gas in the downstream device and the gas mixture 108.

Figure 2:
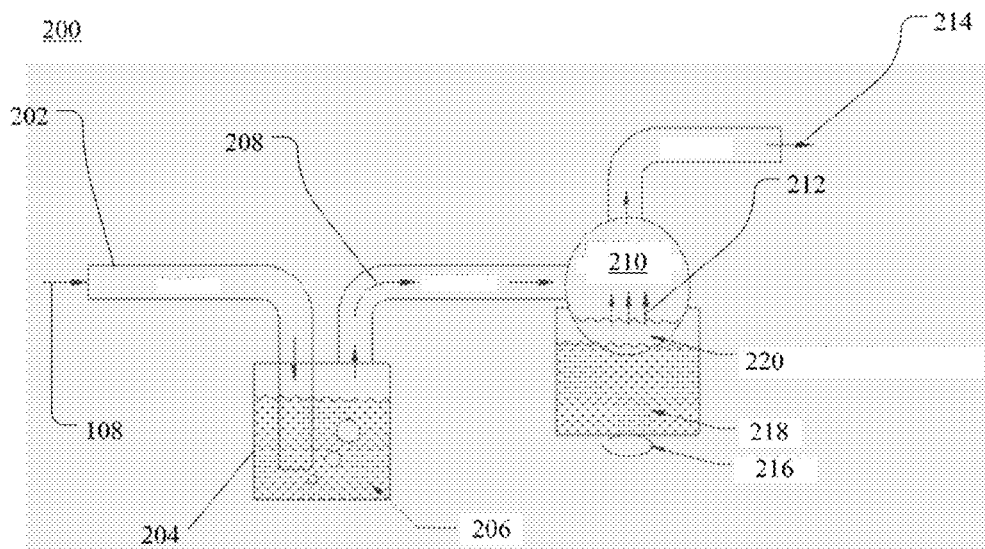
FIG. 2 is a schematic diagram of the gas mixing system in the gas generator for health use according to an embodiment of the invention.

Please refer to FIG. 2, which is a schematic diagram of the gas mixing system in the gas generator for health use according to a preferred embodiment of the invention. The gas mixing system 200 is coupled to the electrolysis device 100 in FIG. 1, such as via a line 202, to receive the gas mixture 108. The gas mixing system 200 comprises a humidifier 204, such as a water tank or a pure water tank, where the gas mixture 108 is introduced into water or pure water 206, so that the gas mixture 108 is filtered to produce a filtered gas 208. In other embodiments, the humidifier 204 is used to eliminate the gaseous impurity produced during the electrolysis, such as chlorine, while leaving the hydrogen and oxygen in the mixed gas mixture 108. It is obvious that this humidifier 204 could be used for reducing or cooling down the temperature of the gas mixture 108 through the help of the water in humidifier 204. Of course, the humidifier 204 is not limited to the pure water tank mentioned in the embodiment above and can also be any other device that is capable of absorbing impurities and gasses other than oxygen and hydrogen. The gas mixing system 200 further comprises an atomized/volatile gas mixing tank 210, coupled to the humidifier 204 to receive the filtered gas 208, where the health gas 214 is produced by mixing the filtered gas 208 and the atomized gas 212. The atomized/volatile gas mixing tank 210 further comprises an oscillator 216, adapted to atomize or volatilize a base liquid 218 and the liquid 220 in the atomized/volatile gas mixing tank 210, producing the atomized gas 212. Preferably, the base liquid 218 is pure water. The liquid 220 is selected from a group consisting of an essential oil, a medicinal liquid, pure water and a combination thereof. That is, the liquid 220 could be an essential oil, a medicinal liquid, pure water, or a combination of two or three of above-mentioned liquids. The atomized gas 212 thus produced is preferably a volatile essential oil, an atomized medicinal liquid, atomized water vapor or a combination of two or three of above-mentioned volatile/atomized items.

Figure 3:
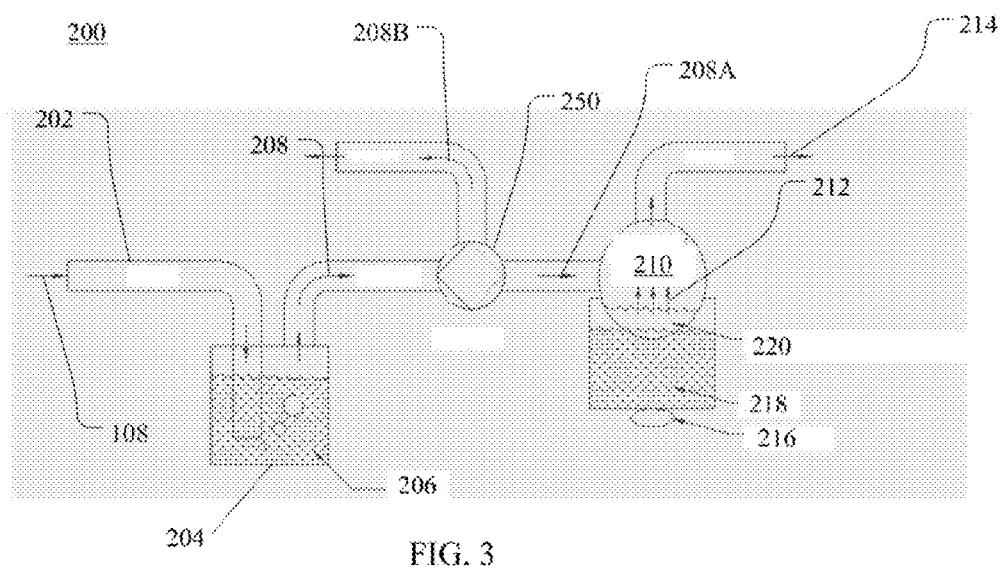
FIG. 3 is a schematic diagram of the gas mixing system in the gas generator for health use according to another embodiment of the invention.

Please refer to FIG. 3, which is a schematic diagram of the gas mixing system in the gas generator for health use according to another embodiment of the present invention. The gas generator for health use further comprises a conversion valve 250, coupled between the humidifier 204 and the atomized/volatile gas mixing tank 210, wherein the conversion valve 250 is configured to selectively connecting the humidifier 204 to the atomized/volatile gas mixing tank 210 to mix the atomized gas 212 and the filtered gas 208A and produce the health gas 214. The conversion valve 250 is adapted to selectively disconnecting the humidifier 204 from the atomized/volatile gas mixing tank 210, so that the filtered gas 208B can be directly withdrawn as the health gas. In other words, a user can decide whether the volatile essential oil, atomized medicine and atomized water vapor are to be introduced or not by switching the conversion value 250. This structural arrangement allows the user to choose to inhale the health gas composed only of the gas mixture of oxygen and hydrogen, which is different from the embodiment of FIG. 2.

In other embodiments, the composition of the health gas is selected by other means than that described above. For example, the user can turn on/off the oscillator 216 to select the composition of the health gas. To elaborate, when the oscillator 216 is turned on, the health gas 214 is produced by mixing the atomized gas 212 and the filtered gas 208. When the oscillator 216 is turned off, no atomized gas is produced and, in this case, the health gas 214 comprises only the filtered gas 208. The use of the on/off switch of the oscillator in the gas mixing system allows a user to choose different types of healthy gases for inhalation.

According to the above embodiments, the health gas 214 comprises hydrogen and oxygen, and optionally a volatile essential oil, an atomized medicine, water vapor or a combination thereof. Studies have found that there is an instable oxygen species (O+), also known as free radicals, in the human body. The free radicals are usually generated due to diseases, diet, environment and one's life style, and the free radicals in the human body can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. In addition, according to the clinical studies, the atomized medicinal liquid is easier absorbed by the human body than its non-atomized counterpart. That is to say, compared with its non-atomized counterpart, the atomized medicine can achieve the same therapeutic effect with a much lower dosage amount. Furthermore, the drug's side effects can be reduced due to the low dosage amount of the atomized medicine administered. Therefore, the health gas 214 may lead to an excellent therapeutic effect. There are also clinical experiments showing that, for patients who need to inhale a high concentration of oxygen for a long time, the lung damage from the high concentration of oxygen can be ameliorated by inhaling hydrogen. Aside from those benefits, the volatile essential oil in the health gas can help general users improve their health and relieve stress.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:

1. A gas generator for health use, comprising:
   an electrolysis device for electrolyzing water to produce a gas mixture including hydrogen and oxygen;
   a gas feeding element, coupled between the electrolysis device and the gas mixing system to feed an additional gas to the gas mixture; and
   a gas mixing system, coupled to the electrolysis device to receive the gas mixture and to mix the gas mixture with an atomized gas selected from a group consisting of an atomized medicinal liquid, a volatile essential oil and a combination thereof to produce a health gas.

2. The gas generator for health use of claim 1, wherein the gas mixing system further comprises:
   a humidifier, coupled to the electrolysis device to receive the gas mixture for producing a filtered gas; and
   an atomized/volatile gas mixing tank, coupled to the humidifier to receive the filtered gas, wherein the atomized/volatile gas mixing tank generates the atomized gas and produces the health gas by mixing the atomized gas and the filtered gas.

3. The gas generator for health use of claim 2, further comprising a conversion valve, coupled between the humidifier and the atomized/volatile gas mixing tank, wherein the conversion valve is adapted to selectively connect the humidifier to the atomized/volatile gas mixing tank, so that the atomized gas and the filtered gas is mixed to produce the health gas and is adapted to selectively disconnect the humidifier from the atomized/volatile gas mixing tank, so that the filtered gas is directly output for being inhaled by a user.

4. The gas generator for health use of claim 2, wherein the atomized/volatile gas mixing tank further comprises an oscillator for atomizing or vaporizing a liquid to produce the atomized gas.

5. The gas generator for health use of claim 4, wherein the liquid is selected from a group consisting of an essential oil, a medicinal liquid, pure water and a combination thereof.

6. The gas generator for health use of claim 5, wherein the atomized/volatile gas mixing tank further comprises a base liquid, wherein the liquid resides on top of the base liquid and the oscillator is set below the base liquid.

7. The gas generator for health use of claim 4, wherein the gas mixing system is configured to selectively output the filtered gas or the health gas by turning on or turning off the oscillator.

8. A gas generator for health use, comprising:
   an electrolysis device for electrolyzing water to produce a gas mixture including hydrogen and oxygen;
   a gas feeding element, coupled between the electrolysis device and the gas mixing system to feed an additional gas to the gas mixture; and
   a gas mixing system, coupled to the electrolysis device to receive the gas mixture and mix the gas mixture with an atomized gas to produce a health gas, wherein the atomized gas is a water vapor, an atomized medicinal liquid, a volatile essential oil, or a combination of any two or three of the water vapor, the atomized medicinal liquid and the volatile essential oil.

9. The gas generator for health use of claim 8, further comprising a flow meter coupled to the electrolysis device for detecting the flow rate of the gas mixture and controlling the quantity of the gas mixture produced from the electrolysis device.

10. The gas generator for health use of claim 9, wherein the flow meter is adapted to cut off electric voltage or electric current supplied to the electrolysis device.

11. The gas generator for health use of claim 8, further comprising a flow controller coupled to the electrolysis device to control the flow rate of the gas mixture flowing into the gas mixing system.

12. The gas generator for health use of claim 8, wherein the additional gas is fed to the gas mixture for reducing the concentration of hydrogen in the gas mixture, wherein the additional gas is selected from a group consisting of air, water vapor, an inert gas, oxygen and a combination thereof.

13. The gas generator for health use of claim 12, wherein the concentration of hydrogen in the health gas ranges from 2% to 60%.

14. The gas generator for health use of claim 8, wherein the electrolysis device comprises two electrodes and the electrodes have interchangeable polarity.

15. The gas generator for health use of claim 8, wherein the gas mixing system comprising a atomized/volatile gas mixing tank which comprises an oscillator for atomizing or vaporizing a liquid to produce the atomized gas.

16. The gas generator for health use of claim 15, wherein the liquid is an essential oil, a medicinal liquid, pure water, or a combination of any two or three of the essential oil, the medicinal liquid, and the pure water.

* * * * *